US008417012B2

(12) United States Patent
Ramirez et al.

(10) Patent No.: US 8,417,012 B2
(45) Date of Patent: Apr. 9, 2013

(54) NON-LINEAR HISTOGRAM SEGMENTATION FOR PARTICLE ANALYSIS

(75) Inventors: Carlos A. Ramirez, Miami, FL (US); Jaesang Park, Miami, FL (US); Jiuliu Lu, Homestead, FL (US)

(73) Assignee: Beckman Coulter, Inc., Brea, CA (US)

( * ) Notice: Subject to any disclaimer, the term of this patent is extended or adjusted under 35 U.S.C. 154(b) by 762 days.

(21) Appl. No.: 12/608,756

(22) Filed: Oct. 29, 2009

(65) Prior Publication Data

US 2010/0111400 A1 May 6, 2010

Related U.S. Application Data

(60) Provisional application No. 61/111,091, filed on Nov. 4, 2008.

(51) Int. Cl.
*G06K 9/00* (2006.01)
(52) U.S. Cl. ......... 382/133; 382/199; 382/170; 382/171
(58) Field of Classification Search ........................ None
See application file for complete search history.

(56) References Cited

U.S. PATENT DOCUMENTS

| | | | |
|---|---|---|---|
| 4,661,913 A | | 4/1987 | Wu et al. |
| 4,907,156 A | * | 3/1990 | Doi et al. ....................... 382/130 |
| 2001/0008562 A1 | * | 7/2001 | Rogers et al. ................. 382/132 |
| 2002/0029235 A1 | * | 3/2002 | Lock et al. .................... 708/814 |
| 2003/0086608 A1 | * | 5/2003 | Frost et al. .................... 382/173 |
| 2006/0263833 A1 | | 11/2006 | Loken et al. |

FOREIGN PATENT DOCUMENTS

| | | |
|---|---|---|
| WO | WO 01/85914 A2 | 11/2001 |
| WO | WO 03/098522 A1 | 11/2003 |

OTHER PUBLICATIONS

The International Search Report Cited in International Application No. PCT/US2009/062992, dated Feb. 11, 2010.
The Written Opinion of the International Searching Authority Cited in International No. PCT/US2009/062992, dated Feb. 11, 2010.

* cited by examiner

*Primary Examiner* — Andrew W Johns
*Assistant Examiner* — Siamak Harandi
(74) *Attorney, Agent, or Firm* — K&L Gates LLP; Louis C. Cullman; Andrew L. Reibman

(57) ABSTRACT

Systems and methods for non-linear histogram segmentation for particle analysis are provided. In one embodiment, a method for analyzing particles comprises creating an initial two-dimensional histogram based on two selected parameters of the particles, filtering the initial two-dimensional histogram to generate a filtered two-dimensional image, detecting a plurality of seed populations in the filtered two-dimensional image, generating one or more linear contour lines, each having a plurality of contour points, to separate the detected seed populations, and adjusting the contour points in at least one of the linear contour lines to separate the detected seed populations.

39 Claims, 17 Drawing Sheets

NON-LINEAR HISTOGRAM SEGMENTATION FOR PARTICLE ANALYSIS

CROSS-REFERENCE TO RELATED APPLICATIONS

The present application claims the benefit of U.S. Provisional Application No. 61/111,091, filed Nov. 4, 2008, which is incorporated by reference herein in its entirety.

FIELD OF THE INVENTION

Embodiments of the present invention generally relate to systems and methods of particle analysis and grouping. More particularly, embodiments of the present invention relate to systems and methods for classifying particles using two dimensional histograms created from data relating to physical properties of the particles.

BACKGROUND

Particle analyzers, such as hematology analyzers or flow cytometers, process biological samples for particle analysis. They measure physical properties of biological particles in biological samples for analysis. Exemplary physical property measurements are electro-optical measurements. The measured physical properties can be viewed as a multidimensional space. Each dimension in the multidimensional space corresponds to a measured physical property. Particles sharing similar physical properties group into clusters in the multidimensional space. Each cluster corresponds to a specific particle population. Due to the statistical distribution of the particles and the multiple dimensions involved, the process of identifying such clusters by an automated method or algorithm is generally a complex task.

One way to reduce such complexity is to use two-dimensional (2D) projections of the multi-dimensional space to perform classification or differentiation of the particles. For example, FIGS. 1A and 1B illustrate two conventional 2D projections of hematology data for white blood cell subpopulations contained in a normal whole blood sample. For example, the 2D projections can be 2D histograms obtained from multidimensional particle analysis data. A 2D histogram contains a set of two-dimensional bins. Each bin accumulates particle events appearing at the location of the bin. The accumulated value represents the projected particle density or count at the location. For instance, this count can be a count of the number of particles having data values that correspond to the bin location.

In FIG. 1A, image 110 is an orthogonal projection of the hematology data on RLS (rotated light scatter)-DC (direct current) dimensions. In image 110, pixel groups (or clusters) 112, 114, and 116 correspond to leukocyte populations, and in particular to monocytes, neutrophils, and eosinophils respectively. Cluster 118 corresponds to lymphocyte and basophil populations. In FIG. 1B, image 120 is an orthogonal projection of the same hematology data on OP (opacity)-DC dimensions. Opacity is a parameter obtained as a function of DC and RF (radio frequency). In image 120, cluster 122 corresponds to a monocyte population, cluster 124 corresponds to neutrophil, eosinophil and basophil populations, and cluster 128 corresponds to a lymphocytes population.

Conventional algorithms apply a segmentation method to separate the clusters in the 2D projections based on analysis of multiple one-dimensional (1D) histograms. A 1D histogram contains a set of one-dimensional bins accumulating particle events at the locations of the bins along that dimension. The accumulated values represent the particle density or count in that dimension. For example, in one conventional technique, an amplitude analysis is performed on multiple 1D histograms. The analyzing results are combined to produce a 2D segmentation. As shown in FIGS. 1A and 1B, the behavior and relationship among the white blood cell subpopulations is well defined for normal samples.

However, changes in the morphology, internal structure, and maturation process of the biological particles can alter the location, size, and shape of the clusters in a 2D histogram. These changes introduce additional complexity for conventional segmentation processes. This is particularly true when shifting and overlapping among the particle populations occur. For example, FIGS. 2A, 2B, 3A, and 3B illustrate orthogonal projections of data from two abnormal blood samples with heavily overlapped monocyte and neutrophil cell populations. In these figures, images 210 and 310 are orthogonal projections on RLS-DC dimensions and images 220 and 320 are orthogonal projections on OP-DC dimensions. In image 210, cluster 212 corresponds to monocyte and neutrophil populations. Cluster 216 corresponds to an eosinophil population. Cluster 218 corresponds to lymphocyte and basophil populations. In image 220, cluster 222 corresponds to monocyte, neutrophil, eosinophil, and basophil populations and cluster 228 corresponds to a lymphocyte population. In image 310, cluster 312 corresponds to monocyte and neutrophil populations. Cluster 316 corresponds to an eosinophil population. Cluster 318 corresponds to lymphocyte and basophil populations. In image 320, cluster 322 corresponds to monocyte, neutrophil, eosinophil, and basophil populations and cluster 328 corresponds to a lymphocyte population. In this example, the clusters commonly associated with the monocyte and neutrophil populations fall into a transition region Therefore, these populations cannot be consistently identified.

There are two general reasons the events can fall into transition regions, such as region 212 in FIG. 2A, region 222 in FIG. 2B, region 312 in FIG. 3A, and region 322 in FIG. 3B. First, as shown in FIGS. 2A and 2B, the events can correspond to heavily overlapped neutrophil and monocyte populations at regions 212 and 222. Second, as shown in FIGS. 3A and 3B, a single monocyte or neutrophil cluster can shift from its expected locations to regions 312 and 322.

While conventional segmentation approaches work well for normal samples and for some abnormal samples, they perform inconsistently with samples such as those yielding results similar to FIGS. 2A, 2B, 3A and 3B. The main reason for this inconsistent performance is conventional algorithms only rely on a search for peaks and valleys in multiple 1D histograms obtained from the rows and columns of the 2D histogram. As a result, conventional algorithms run into problems, for example, where peaks and valleys have merged together because of populations shifts.

BRIEF SUMMARY OF THE INVENTION

Embodiments of the present invention provide a system and method for segmenting 2D histograms that improves the differentiation and segmentation of overlapping particle populations. The method uses 2D digital image processing techniques to replace the conventional peak and valley analysis of multiple 1D histograms. One feature of the present invention is to segment the 2D histograms directly using non-linear image segmentation techniques, which can provide a more consistent and accurate segmentation of the 2D histograms and better differentiation of overlapping or shifted particle populations.

In one embodiment, the present invention is directed to a method for analyzing biological particles, such as blood cells. Biological particles from the biological sample are passed through a measuring region of a particle analyzer. Each particle passing through the measuring region is interrogated with at least two parameters. The at least two parameters are detected with one or more detectors and stored as data.

Data corresponding to first and second parameters is then selected. The selected data is used to create an initial two-dimensional histogram, wherein a first dimension of the two-dimensional histogram corresponds to the first parameter and a second dimension of the two-dimensional histogram corresponds to the second parameter. The initial two-dimensional histogram is filtered to generate a filtered two-dimensional image. After filtering, a plurality of seed populations are detected in the filtered two-dimensional image. One or more linear contour lines are generated, each having a plurality of contour points to separate the detected seed populations. The generated contour lines are adjusted by adjusting the contour points in at least one of the linear contour lines to separate the detected seed populations.

Another embodiment of the present invention is directed to a device for analyzing particles. The device includes a transducer module having a plurality of interrogation sources to provide electro-optical interrogations of at least one of the particles and having at least one detector to detect at least two parameters corresponding at least one of the particles, and an analysis system. The analysis system includes a memory, a selection module, a histogram creation module, a filter, a seed detection module, an adjustment module, and a separation module. The memory stores data corresponding to parameters detected from the particles. The selection module selects first data corresponding to a first stored parameter and second data corresponding to a second stored parameter. The histogram creation module creates an initial two-dimensional histogram using data corresponding to the first and second parameters, wherein a first dimension of the two-dimensional histogram corresponds to the first parameter, and a second dimension of the two-dimensional histogram corresponds to the second parameter. The filter filters the initial two-dimensional histogram to generate a filtered two-dimensional image. The seed detection module detects a plurality of seed populations in the filtered two-dimensional image. The separation module generates one or more linear contour lines that separate the detected seed populations, each contour line having a plurality of contour points. The adjustment module adjusts the contour points of at least one of the linear contour lines to separate the detected seed populations.

Further embodiments, features, and advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention and, together with the description, further serve to explain the principles of the invention and to enable a person skilled in the pertinent art to make and use the invention.

The present invention is described with reference to the accompanying drawings. The drawing in which an element first appears is typically indicated by the leftmost digit in the corresponding reference number.

Figure 1A:
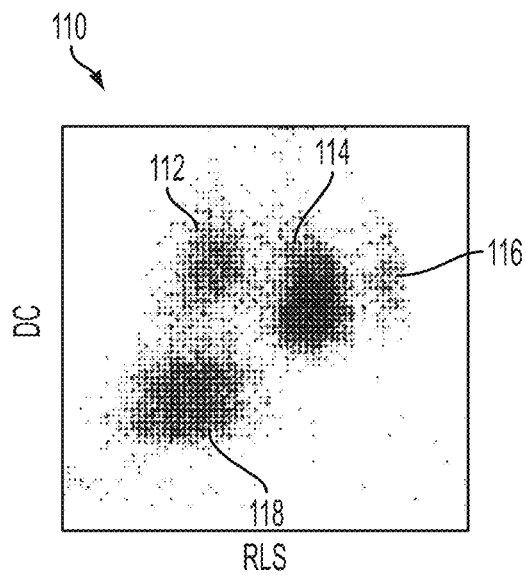
FIGS. 1A and 1B show 2D histograms obtained by orthogonal projections of a normal blood sample data on RLS-DC and OP-DC, respectively.
Figure 1B:
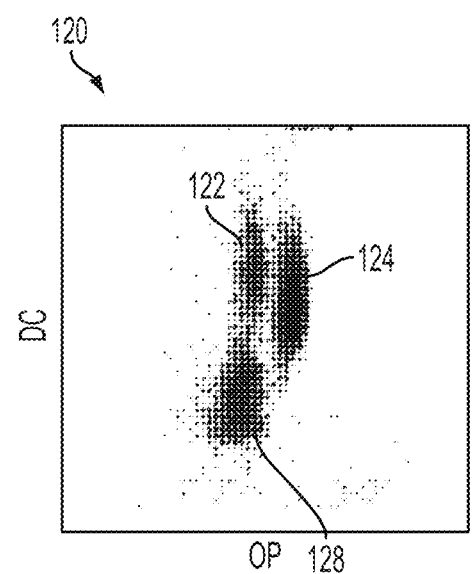
Figure 2A:
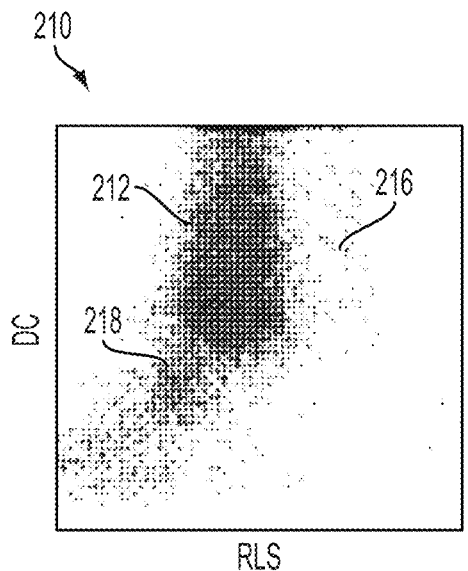
FIGS. 2A and 2B show 2D histograms obtained by orthogonal projections of a first abnormal blood sample data on RLS-DC and OP-DC dimensions.
Figure 2B:
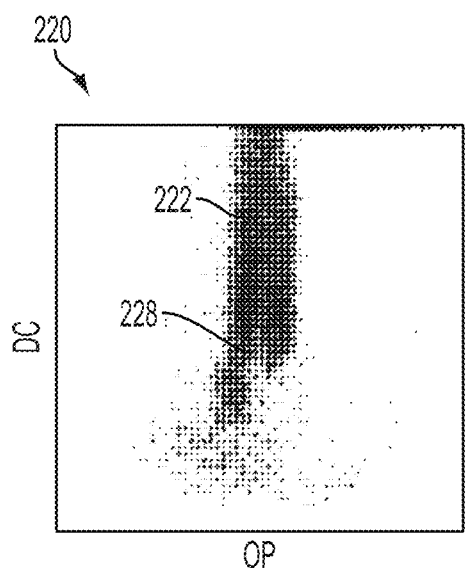
Figure 3A:
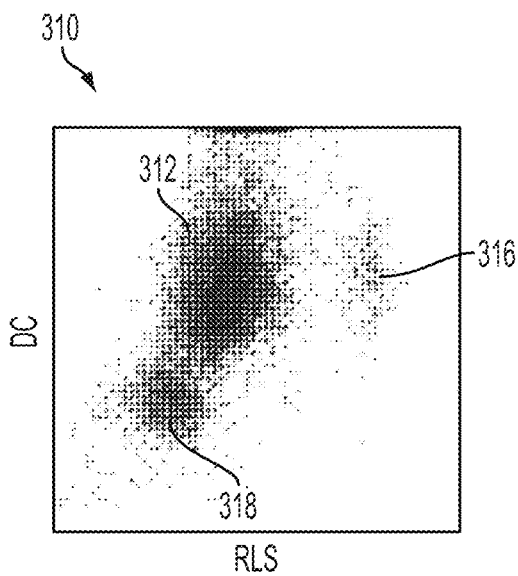
FIGS. 3A and 3B show 2D histograms obtained by orthogonal projections of VCS data for a second abnormal blood sample data on RLS-DC and OP-DC dimensions.
Figure 3B:
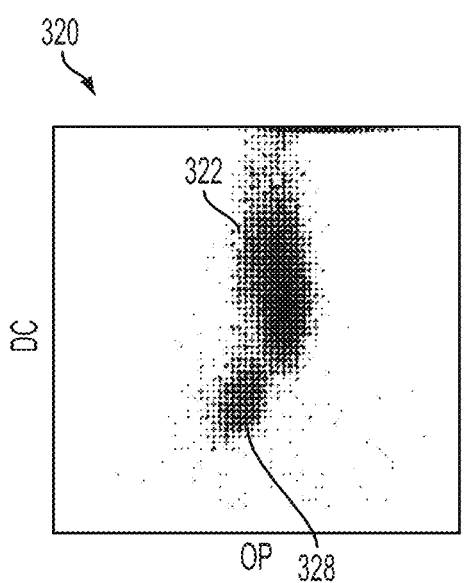
Figure 4A:
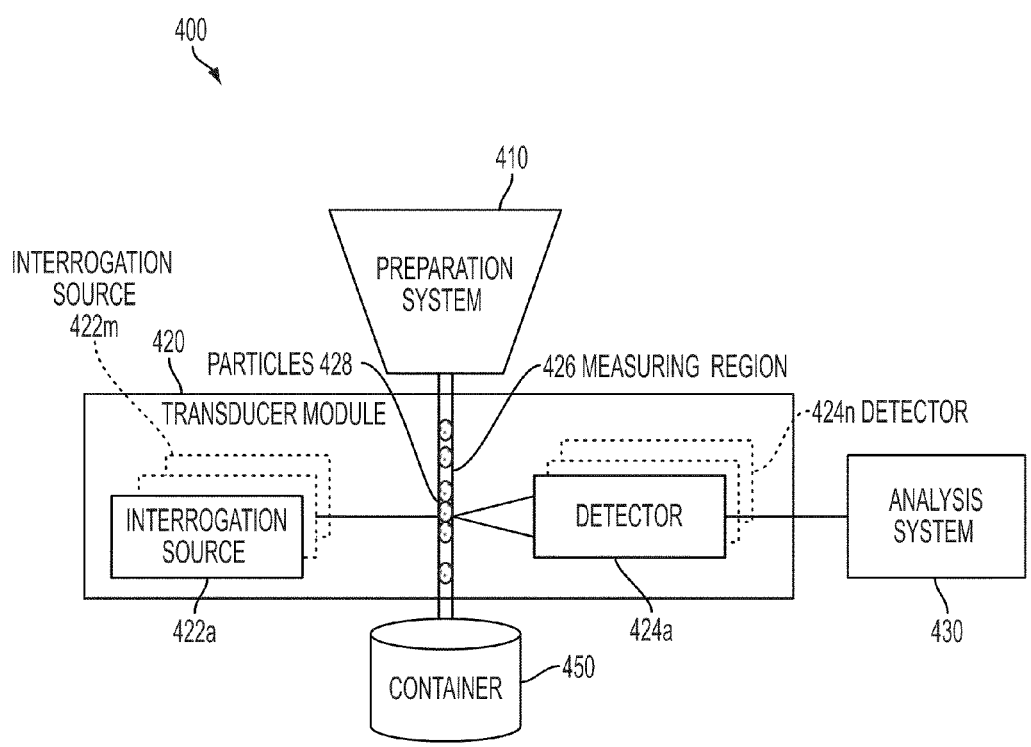
Figure 4B:
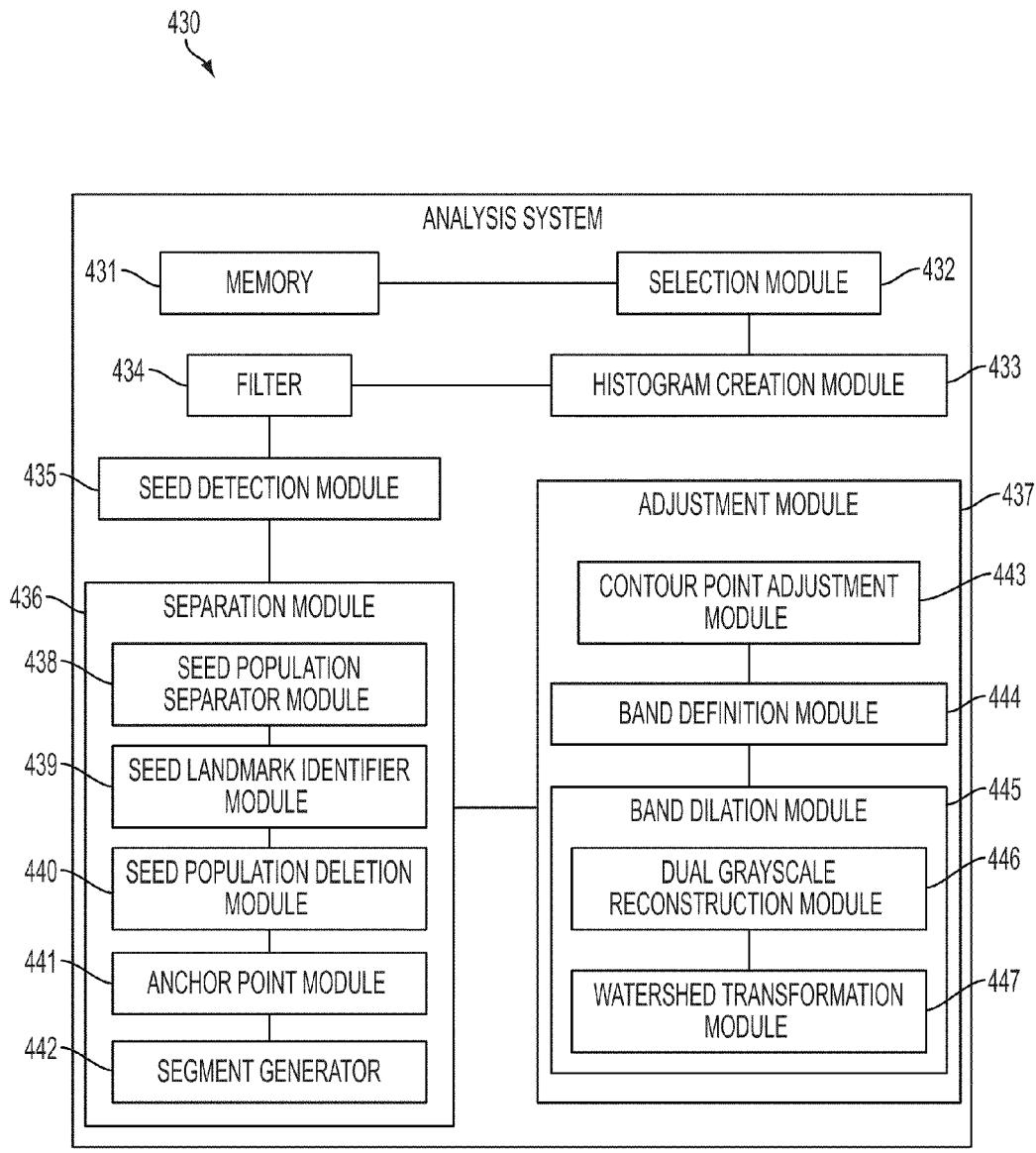
Figure 4C:
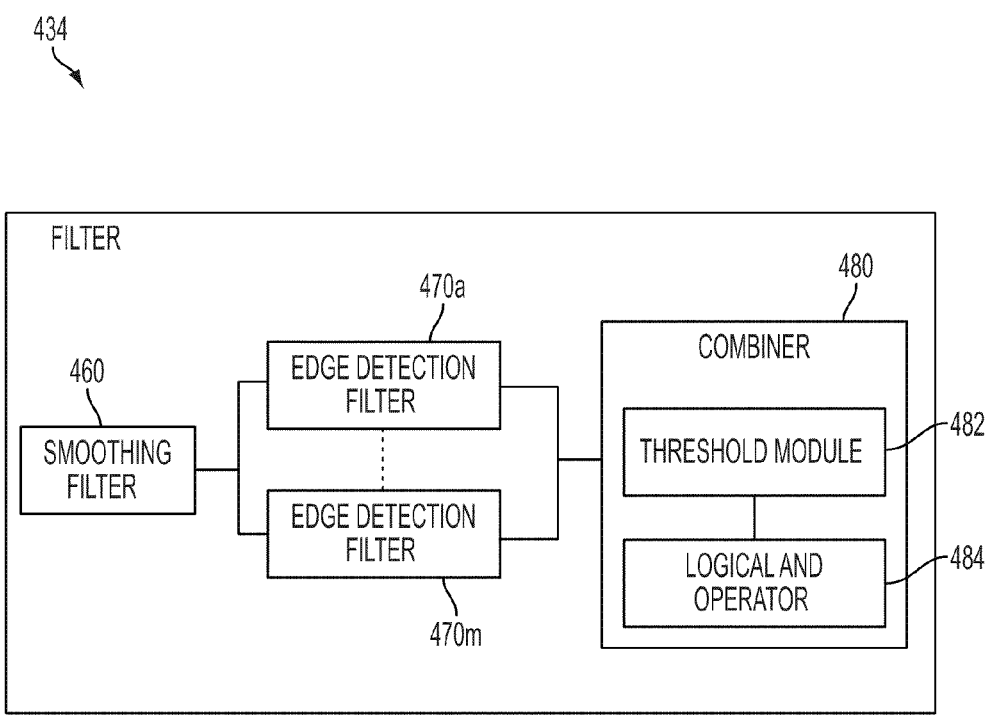

FIGS. 4A-C are exemplary diagrams of a particle analysis system according to an embodiment of the invention.

Figure 5:
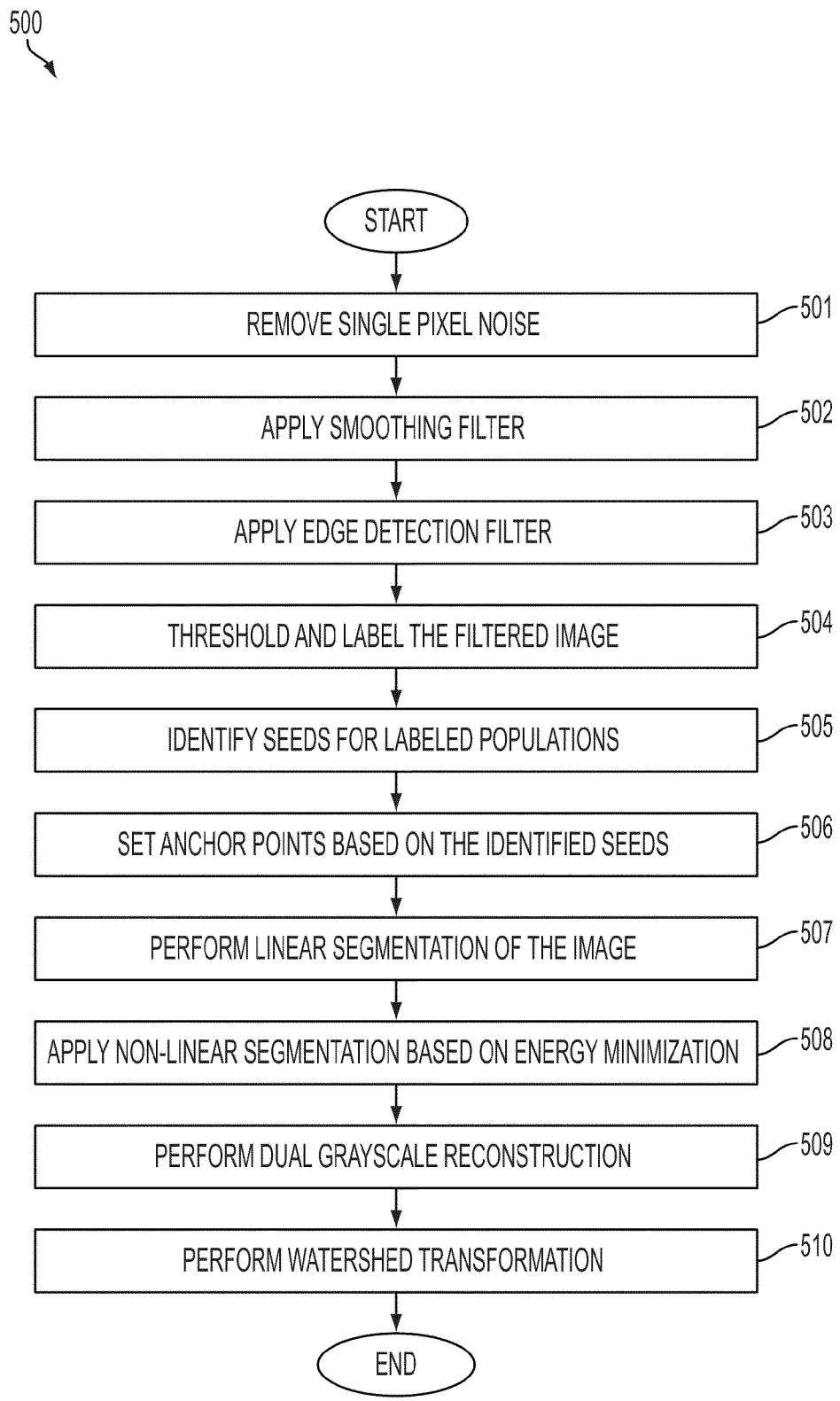

FIG. 5 is a flowchart of an exemplary procedure of a particle analysis method according to an embodiment of the invention.

Figure 6:
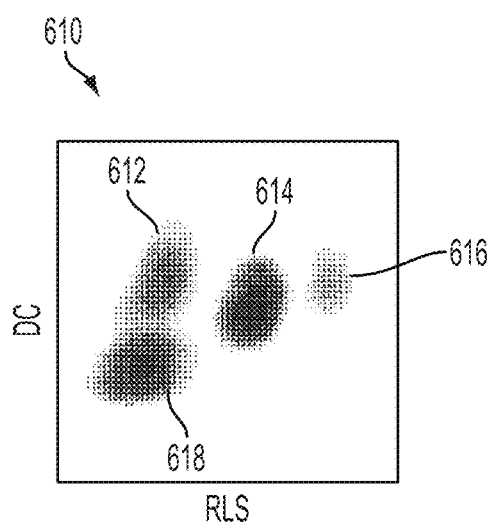

FIG. 6 shows a result of smoothing an RLS-DC histogram according to an embodiment of the present invention.

Figure 7:
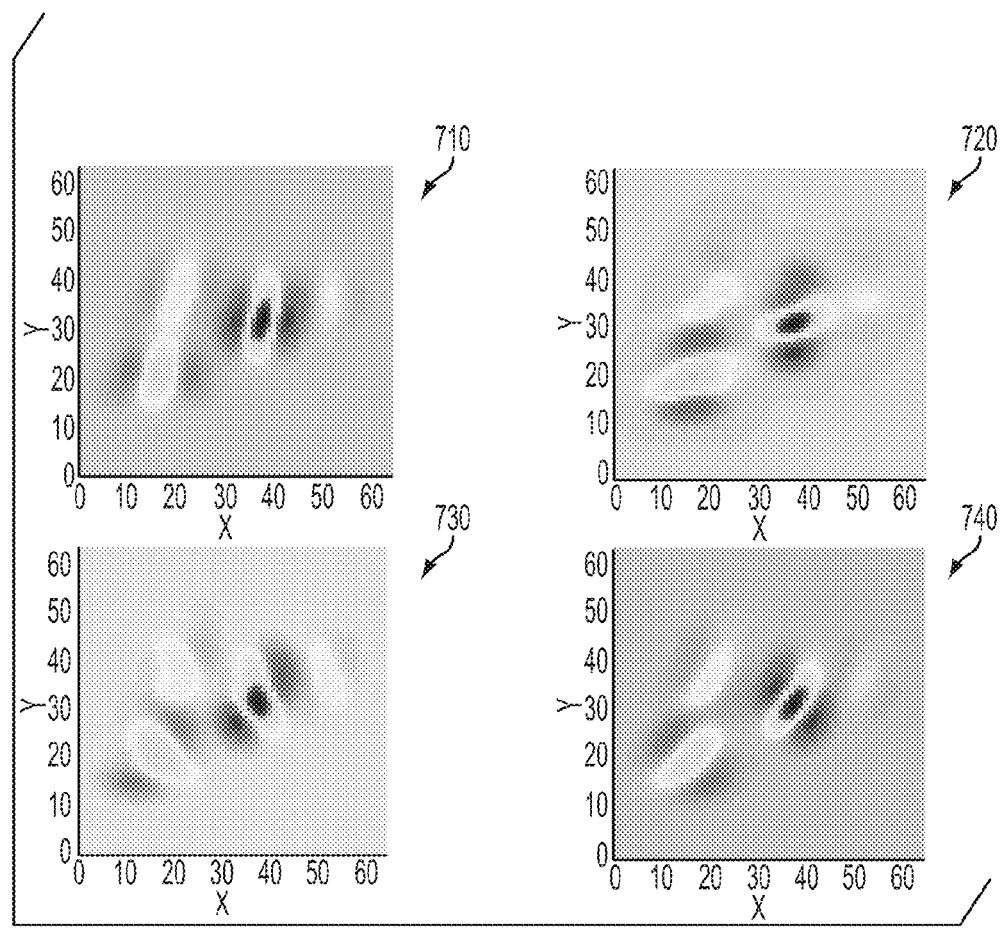

FIG. 7 shows results of applying a horizontal, a vertical, a diagonal LxR and a diagonal RxL directional filter to the smoothed RLS-DC image in FIG. 6 according to an embodiment of the present invention.

Figure 8:
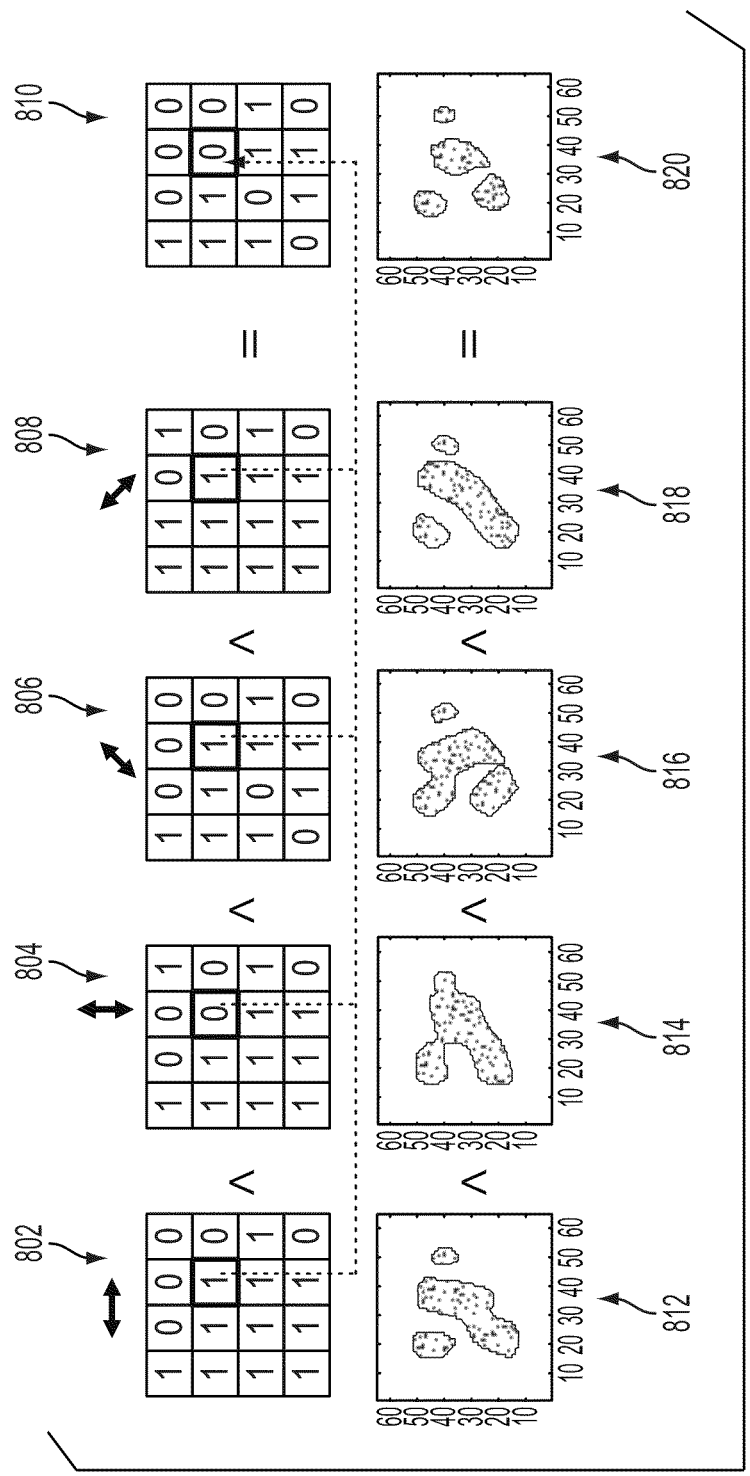

FIG. 8 shows directional image thresholding and corresponding binary images according to an embodiment of the present invention.

Figure 9A:
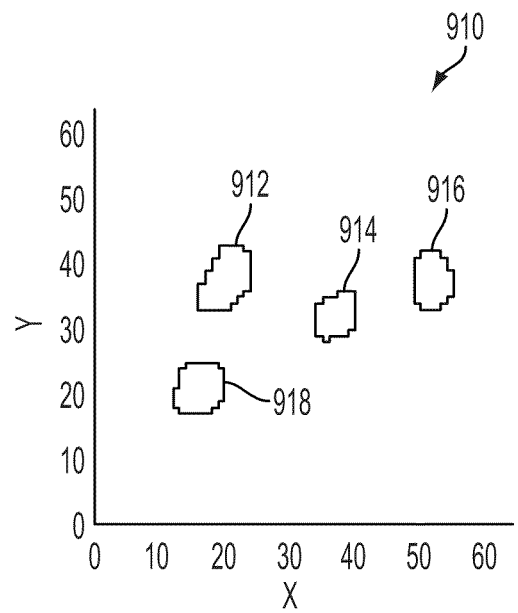
Figure 9B:
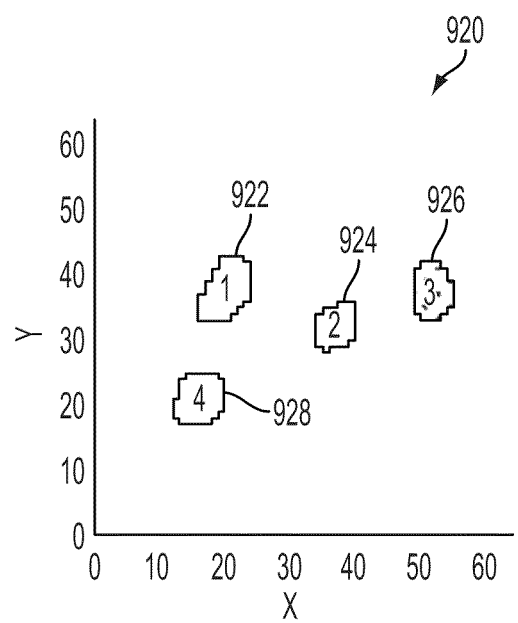

FIGS. 9A and 9B show final RLS-DC seed images after thresholding and labeling respectively according to an embodiment of the present invention.

Figure 10A:
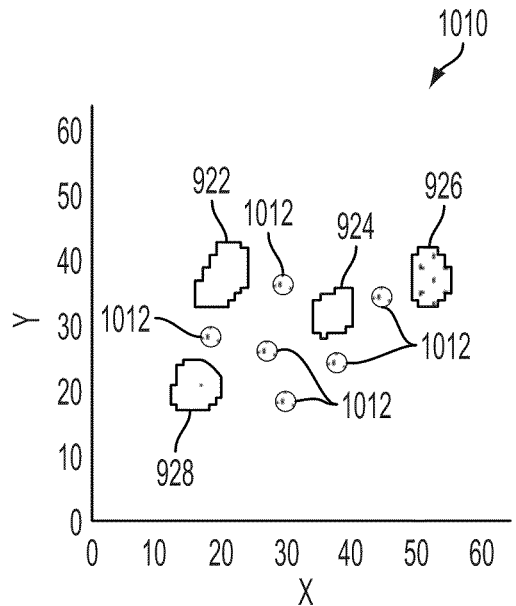
Figure 10B:
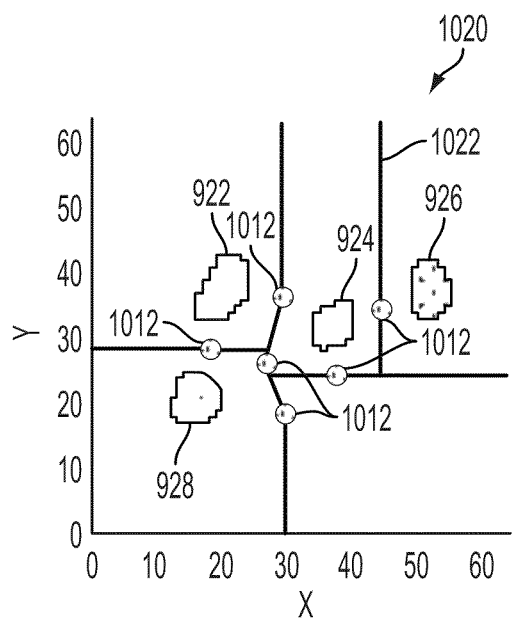

FIG. 10A shows an anchor point setting in the labeled RLS-DC seed image from FIG. 9B and FIG. 10B shows a linear segmentation based on anchor points according to an embodiment of the present invention.

Figure 11:
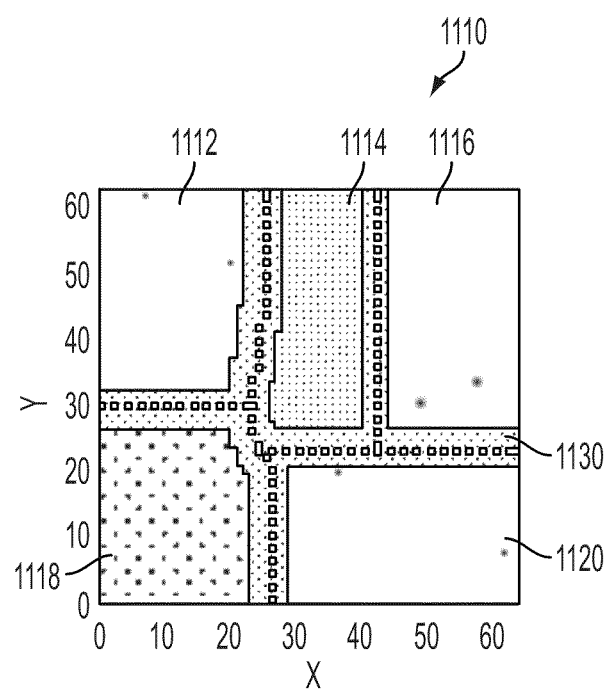

FIG. 11 shows a band image based on contouring points according to an embodiment of the present invention.

Figure 12:
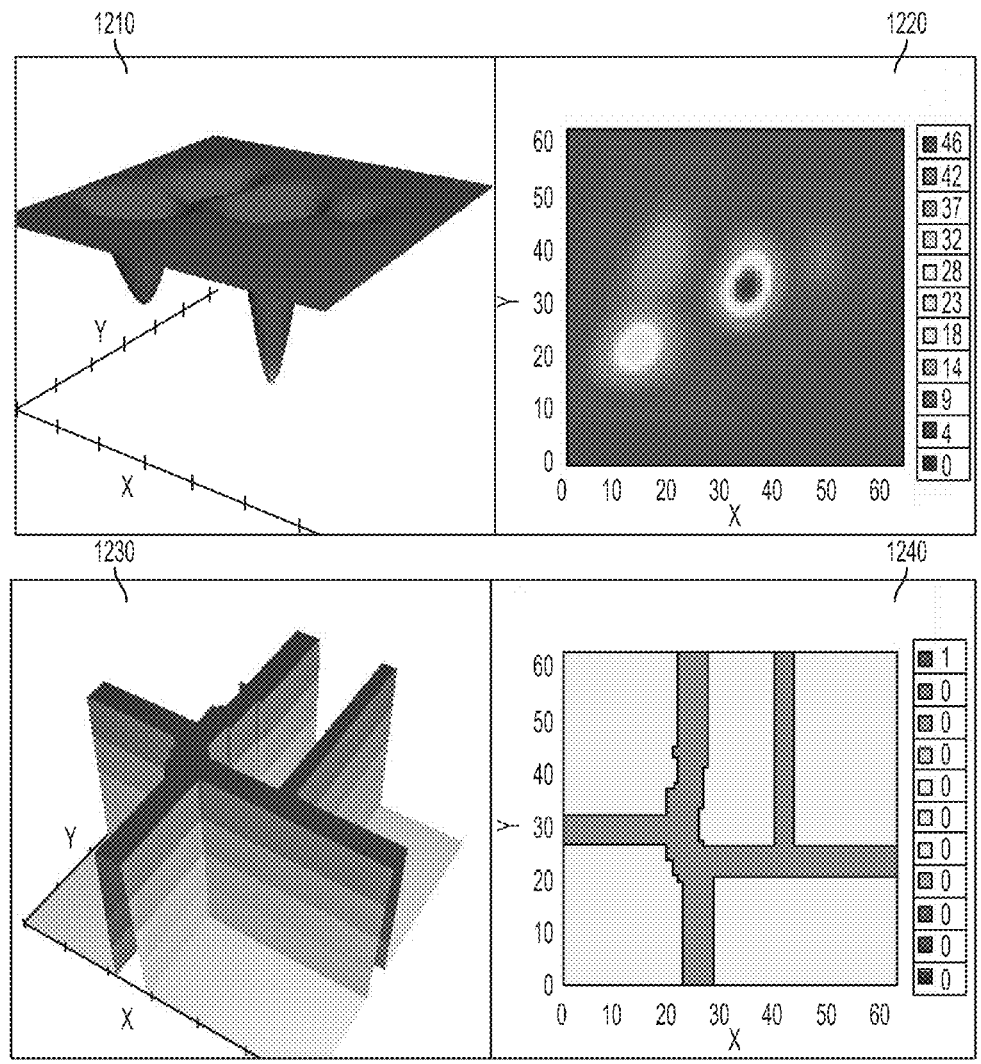

FIG. 12 shows a mask image and a marker image as input to the dual grayscale reconstruction method according to an embodiment of the present invention.

Figure 13A:
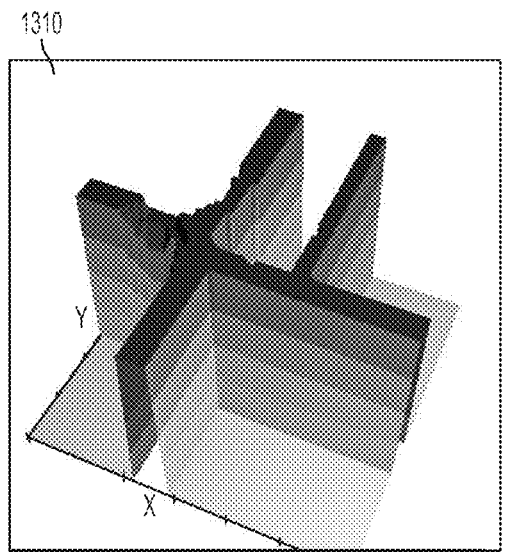
Figure 13B:
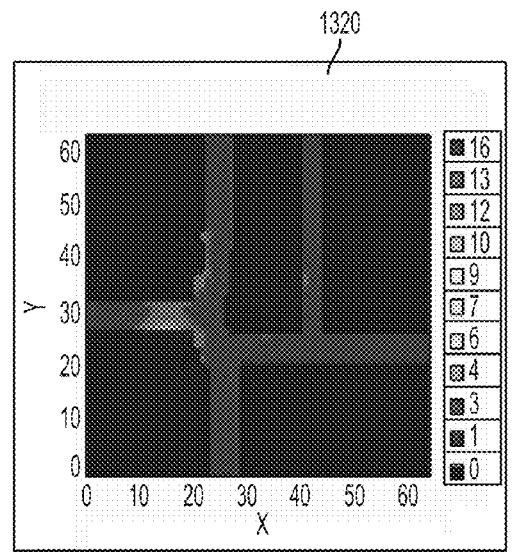

FIGS. 13A and 13B show different views of a dual grayscale reconstructed image using input from FIG. 12 according to an embodiment of the present invention.

Figure 14A:
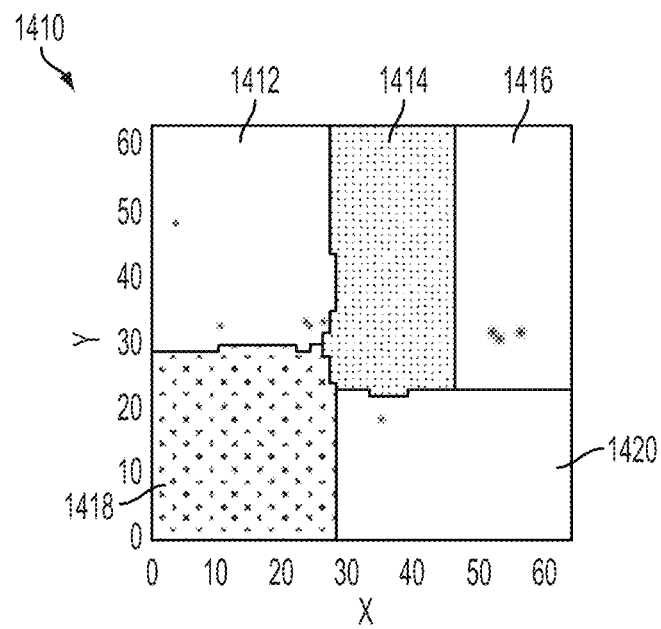

FIG. 14A shows the Watershed transformed 2D image according to an embodiment of the present invention.

Figure 14B:
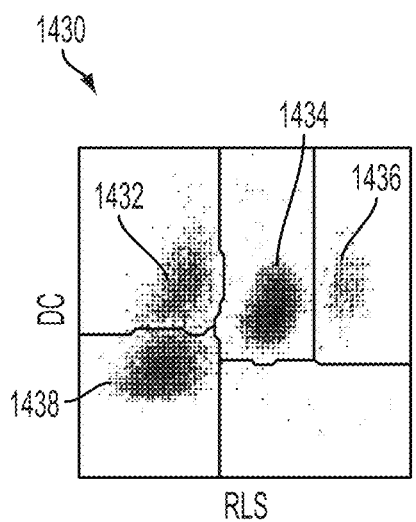

FIG. 14B shows the final result of RLS-DC histogram segmentation, according to an embodiment of the present invention.

Figure 15:
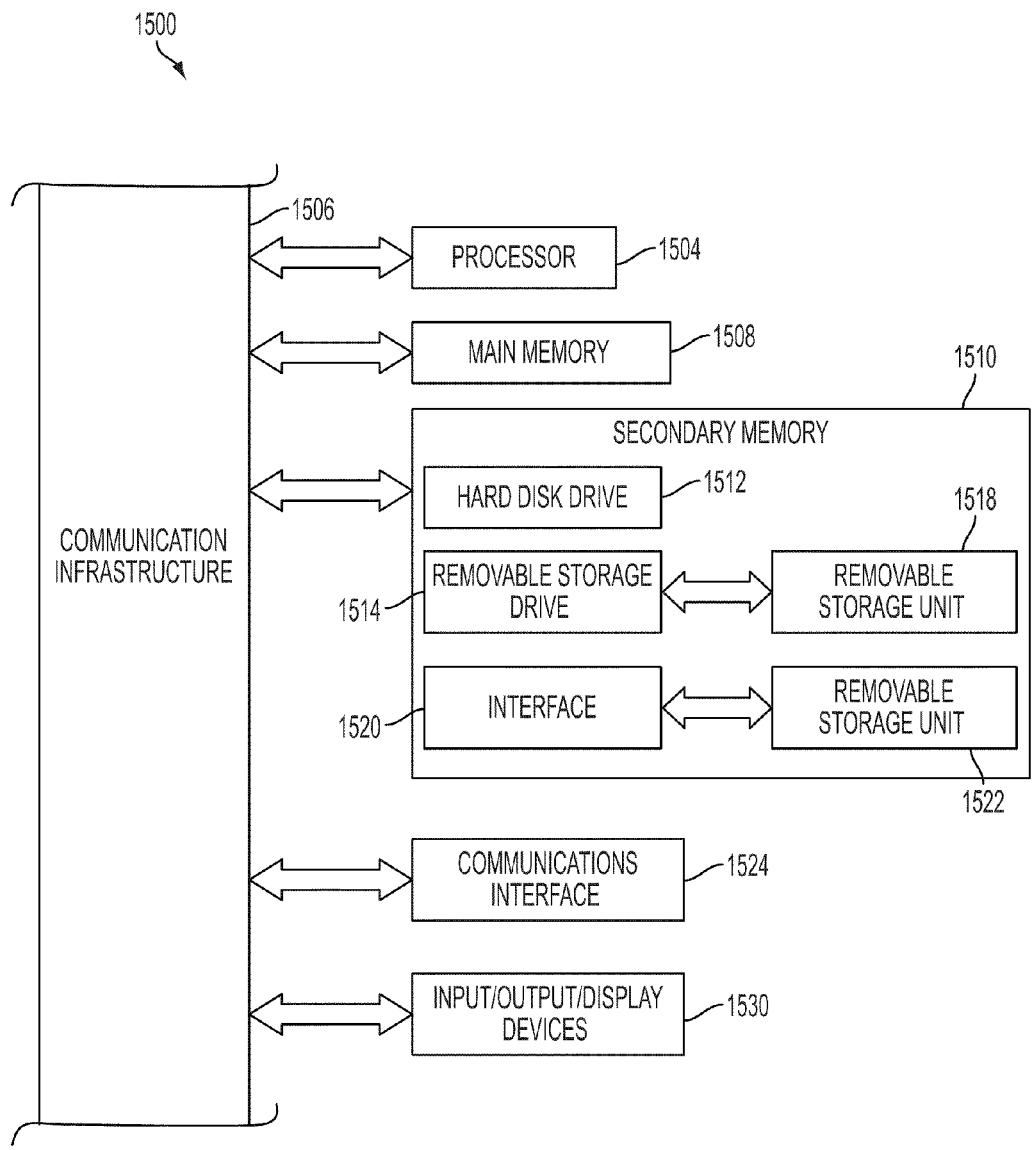

FIG. 15 is a diagram of an exemplary computer system for segmenting two-dimensional histograms according to an embodiment of the present invention.

DETAILED DESCRIPTION OF THE INVENTION

Embodiments of the present invention provide a system and method for segmenting 2D histograms that improve the differentiation and segmentation of overlapping particle populations. The method uses 2D digital image processing techniques to replace conventional peak and valley analysis of multiple 1D histograms alone.

In essence, according to a feature of the present invention, the 2D histogram is treated as an image wherein each pixel has an intensity value proportional to the corresponding histogram bin amplitude.

Embodiments of the present invention are described with respect to hematology analyzers. Hematology analyzers attempt to differentiate blood cell populations. Embodiments of the present invention apply a series of steps for segmenting 2D histograms to optimize this differentiation. Those skilled in the art would recognize the disclosed embodiment are not limited to hematology analyzers or the analysis of blood cells and can be applied in numerous environments to analyze numerous types of particles.

System Overview

In general, to segment particle populations, embodiments of the present invention perform seed detection, anchor point placement, dynamic contouring and morphological fine tuning. In one embodiment of the present invention, for example, the particles are blood cells. In another embodiment, the particles are DNA fragments.

Seed detection refers to detecting regions of local maxima in a 2D histogram. Anchor point placement refers to placement of reference points used to separate particle populations and define the connection points between a linear segmentation. Dynamic contouring and morphological fine tuning refers to fine tuning the linear segmentation, and provides flexibility to the linear segmentation to better separate the particle populations.

Application of these steps results in an optimal non-linear segmentation of the 2D histogram into separate data clusters. As a result, embodiments of the present invention improve the ability to detect overlapped populations in a 2D histogram.

FIGS. 4A-C illustrate schematic diagrams of an exemplary system for particle analysis based on the non-linear 2D histogram segmentation according to one embodiment of the invention. FIG. 4A is a schematic diagram of a system 400 for analyzing particles according to an embodiment of the present invention. System 400 includes a preparation system 410, a transducer module 420, an analysis system 430, and a container 450.

Preparation system 410 prepares biological samples containing particles for analysis. In one embodiment, preparation system 410 mixes a blood sample with a lytic reagent to lyse red blood cells and form a blood sample mixture containing white blood cells. In another embodiment, preparation system 410 prepares a tissue sample that is separated from connective tissue and suspended in a biologically compatible liquid medium that does not destroy the cells. These examples are illustrative and not intended to limit the present invention. In alternative embodiments, other types of biological samples and biological particles may be prepared. Container 450 stores samples passing through transducer module 420 from preparation system 410.

Transducer module 420 provides data corresponding to the particles to be analyzed. In one embodiment, transducer module 420 includes several interrogation sources 422a-m, several detectors 424a-n, and a measuring region 426. Preparation system 410 passes the prepared particles 428 from the biological sample through measuring region 426. Interrogation sources 422a-m provide electro-optical interrogation of particles 428 so that one or more parameters associated with the particles can be detected by detectors 424a-n respectively. In one embodiment, for example, interrogation sources 422a-m may include one or more laser and/or electrical sources. In alternative embodiments, other types and/or numbers of interrogation sources can be used. Detectors 424a-n detect the parameters corresponding to the interrogated particles in the biological sample. Detectors 424a-n then send the parameters to analysis system 430 for analysis. In one embodiment, detectors 424a-n include one or more photodiode sensors. Detectors 424a-n can also include a DC receiver. In alternative embodiments, other types of detectors can be used.

In one embodiment, the parameters are derived from electro-optical measurements, which include DC (direct current), RF (radio frequency), one or more types of light scatter (at one or more angles), fluorescence, and axial light loss as described, for example, in U.S. Pat. No. 5,125,737 which is herein incorporated by reference in its entirety, and others known in the art. These examples of parameters are illustrative and not intended to limit the present invention.

FIG. 4B is a schematic diagram of an exemplary analysis system 430 according to one embodiment of the invention. Analysis system 430 includes a memory 431, a selection module 432, a histogram creation module 433, a filter 434, a seed detection module 435, a separation module 436, and an adjustment module 437. Analysis system 430 can be implemented as software, firmware, hardware, or any combination thereof on a computing device. Example computing devices, include, but are not limited to, a computer, workstation, distributed computing system, embedded system, stand-alone electronic device, networked device, rack server, a device having at least one processor and memory, or other type of computer system.

Memory 431 stores the parameters sent by detectors 424a-n as data. Selection module 432 selects a first data corresponding to a first stored parameter and a second data corresponding to a second stored parameter.

Histogram creation module 433 creates an initial two-dimensional (2D) histogram using the selected data corresponding to the first and second parameters. The first dimension of the 2D histogram corresponds to the first parameter, and the second dimension of the 2D histogram corresponds to the second parameter.

Filter 434 filters the initial 2D histogram so that particle populations in the 2D histogram can be detected. FIG. 4C is a schematic diagram of an exemplary filter 434 according to one embodiment of the invention. In one embodiment, filter 434 includes a smoothing filter 460, one or more edge detection filters 470a-470m, and a combiner 480.

Smoothing filter 460 smoothes the 2D histogram using smoothing filters. In one embodiment, smoothing filter 460 uses Gaussian convolution to smooth the 2D histogram. Other smoothing techniques are known in the art. The smoothed result can be viewed as a 2D image corresponding to the 2D histogram.

Edge detection filters 470a-470m are applied to the smoothed 2D image to detect edges in the image. One embodiment uses edge detection filters based on Laplacian of Gaussian (LoG) filters to generate edge-detected 2D images. It is understood that the LoG filters are merely exemplary of such edge detection filters and reference to them is not intended to limit the present invention.

Combiner 480 combines the edge-detected images to form a final filtered result. In one embodiment, combiner 480 includes a threshold module 482 and a logical AND operator 484. Threshold module 482 uses a threshold filter on each of the edge-detected 2D images to generate corresponding thresholded 2D images. Logical AND operator combines the thresholded 2D images using logical AND operations on a pixel-by-pixel basis to generate a combined thresholded 2D image. In one embodiment, combiner 480 is implemented by combining logic.

Seed detection module 435 detects seed populations in the filtered 2D image. Separation module 436 generates one or more linear contour lines that separate the detected seed populations. Each contour line has a set of contour points.

In one embodiment, separation module 436 includes a seed population separator module 438, a seed landmark identifier module 439, a seed population deletion module 440, an anchor point module 441, and a segment generator 442.

Seed population separator module 438 separates the detected seed populations into groups. Seed landmark identifier module 439 identifies a landmark seed population in each group. Seed population deletion module 440 deletes those seed populations in each group that are not the landmark seed populations. Anchor point module 441 determines one or more anchor points for defining the contour lines. Segment generator 442 generates linear segments of contour lines to separate the seed populations.

Adjustment module 437 adjusts the contour points of the linear contour lines to separate the detected seed populations. In one embodiment, adjustment module 437 includes a contour point adjustment module 443, a band definition module 444, and a band dilation module 445.

Contour point adjustment module 443 adjusts the contour points to minimize an energy function. In one embodiment, the energy function is based on the energy minimization of active contours. In alternative embodiments, other energy functions can be used. Band definition module 444 defines a band around each contour point. Band dilation module 445 then dilates each defined band around each contour point.

In one embodiment, band dilation module 445 includes a dual grayscale reconstruction module 446 and a Watershed transformation module 447. Dual grayscale reconstruction module 446 performs dual grayscale reconstruction on the 2D image. Watershed transformation module 447 then applies a Watershed transformation on the resulting 2D image to segment the image.

2D Histogram Generation

To analyze particles based on 2D histogram segmentation, first a sample containing the particles is provided. In one embodiment, preparation system 410 provides samples containing the particles. Transducer module 420 then provides electro-optical interrogation of the particles in the samples using one or more interrogation sources such as interrogation sources 422a-422m. Detectors 424a-n detect and measure the parameters of the particles in the samples and send the parameters to analysis system 430. Analysis system 430 stores the parameters as data in memory 431. To create a 2D histogram corresponding to the data, selection module 432 selects data corresponding to two of the parameters. Histogram creation module 433 then creates 2D histograms using the selected data, where the two dimensions in the histograms correspond to the two parameters, respectively.

Once the 2D histograms are generated, they can be segmented by analysis system 430. FIG. 5 shows a flowchart diagram of an exemplary routine 500 for particle analysis using non-linear 2D histogram segmentation according to one embodiment of the invention (steps 501-510).

Seed Detection

The first step for segmenting 2D histograms is seed detection (steps 501 through 504 in FIG. 5). Seed detection attempts to detect regions of local maximum amplitude in a 2D histogram. Each detected local maximum amplitude is referred to as a "seed." In one embodiment of the present invention, seed detection is performed by seed detection module 435 and includes three stages: Smoothing, Filtering and Labeling.

Smoothing

In the smoothing stage, single-pixel noise in the 2D histogram is first removed in step 501. Single-pixel noise refers to noise that can be attributed to pixels individually. One example of single-pixel noise is salt-and-pepper noise. The term "salt and pepper noise" refers to single pixel noise statistics.

In one embodiment, "salt and pepper" noise is removed in two steps.

In the first step, each pixel's nearest neighbors are analyzed. Clusters are created by grouping all neighboring non-zero pixels. If a pixel does not have a non-zero pixel neighbor, the pixel forms a single-pixel cluster.

In the second step, for each cluster, the number of pixels in the cluster and the maximum number of events among the pixels inside the cluster are computed. If a cluster does not have at least a specified number of pixels and its maximum number of events is less than a specified value, the pixels in the cluster are removed. In one embodiment, pixels are removed by setting the pixel value to zero. In one embodiment, the specified number of pixels is three. The specified number of pixels can be predetermined or user-specified. Similarly, the specified value of maximum number of events for a cluster can also be predetermined or user-specified. In one example, the specified value for a maximum number of events is fairly low. For example, this can be 1 or 2 events, less than 10 events, or other value depending upon a particular application.

In another embodiment, "salt and pepper" noise is removed by first analyzing the nearest neighbors of each pixel. Pixels that don't have at least a specified number of nearest neighbors having non-zero values are removed. In one embodiment, pixels are removed by setting the pixel value to zero. In one embodiment, the number of nearest non-zero-value neighbors is four. The number of nearest neighbors can be predetermined or user-specified. Second, the number of events in each pixel is checked. Pixels not having at least a particular number of events are considered noise and removed. The number of events each pixel must have can be predetermined or user-specified.

In one embodiment, pixels on the edges in the 2D histogram will not be removed and are kept for other analysis.

In alternative embodiments, other techniques, for example, median filters, can be used to remove single pixel noise. The above examples are strictly illustrative and are not intended to limit the present invention.

After removal of the single pixel noise, in step 502, the resulting 2D image is further smoothed by smoothing filter 460 in filter 434 of system 400. In one embodiment, smoothing filter 460 is based on Gaussian convolution using a Gaussian kernel defined by equation (1):

$$G(x, y) = \frac{1}{2\pi\sigma^2} e^{-(x^2+y^2)/(2\sigma^2)} \quad (1)$$

As used herein the term "kernel" refers to a matrix data structure type (or window) usually containing parameters of a digital filter. An image can be filtered by applying a kernel matrix on each pixel of the image. In equation (1), x and y represent the pixel coordinates in an image. $\sigma$ represents the width of the kernel, which determines the local influence of neighboring pixels to the center of the kernel. Larger values of $\sigma$ can result in lower resolutions of the seed image. In other words, larger values of $\sigma$ will produce less seeds in the image. Similarly, smaller values of $\sigma$ will produce more seeds in the image. For example, $\sigma=9$ can produce less seeds in the image than $\sigma=3$.

The kernel can be successively convoluted with the resulting 2D image several times. The number of times the kernel is convoluted with the image dictates how "smooth" the image looks. FIG. 6 shows an example 610 of a smoothed 2D image on RLS-DC measurements using Gaussian convolution. In image 610, clusters 612, 614, and 616 correspond to monocyte, neutrophil, and eosinophil populations respectively. Cluster 618 corresponds to lymphocyte and basophil populations.

Smoothing using the kernel can be performed any number of times, depending on the particular application. For example, to identify high-level features, more smoothing is performed, e.g., five or six passes with the kernel. To maintain higher resolution, on the other hand, less smoothing is performed.

Filtering

The next stage of seed detection is filtering for edge detection by edge detection filters 470a through 470m in step 503. The filters in step 503 detect changes in the gradient of the image in a particular direction so that edges in the image can be detected. For 2D histograms, the edges can indicate boundaries of different populations.

In one embodiment, the resulting image after smoothing is convolved with four directional 2D Laplacian of Gaussian (LoG) filters in horizontal, vertical, and two diagonal directions:

$$Horizontal = \begin{bmatrix} 0 & 0 & 0 \\ 1 & -2 & 1 \\ 0 & 0 & 0 \end{bmatrix} \quad (2)$$

$$Vertical = \begin{bmatrix} 0 & 1 & 0 \\ 0 & -2 & 0 \\ 0 & 1 & 0 \end{bmatrix} \quad (3)$$

$$DiagonalL \times R = \begin{bmatrix} 1 & 0 & 0 \\ 0 & -2 & 0 \\ 0 & 0 & 1 \end{bmatrix} \quad (4)$$

$$DiagonalR \times L = \begin{bmatrix} 0 & 0 & 1 \\ 0 & -2 & 0 \\ 1 & 0 & 0 \end{bmatrix} \quad (5)$$

For example, FIG. 7 shows the result of applying each directional filter to the smoothed image in FIG. 6. In FIG. 7, plots 710, 720, 730, and 740 are results corresponding to the direction filters in (2), (3), (4), and (5) respectively. In alternative embodiments, other types of edge detection filters can be used.

Thresholding and Labeling

The edge-detected 2D images are thresholded and labeled to generate a final seed image in step 504. In one embodiment, thresholding is performed by combiner 480. As seen in FIG. 8, the final seed image is the result of thresholding the images using threshold module 482 and applying logical AND operator 484 to the resulting binary images to produce a single image. In FIG. 8, matrices 802, 804, 806, and 808 illustrate exemplary sample pixel values in a subsection of the edge-detected images after thresholding, and plots 812, 814, 816, and 818 illustrate thresholded 2D images. Plots 810 and 820 are the combined sample pixels values and resulting single image respectively after the logic AND operation.

Thresholding is performed by picking a threshold value and discarding all pixels in the resulting image that have a value below the threshold value. For example, in one embodiment, amplitude values of pixels above the threshold are set to one and the rest are set to zero in the 2D image. The threshold can be predetermined or user-specified. For example, in one embodiment, the threshold is selected as 0.

After thresholding, the thresholded images are combined by logical AND operation of each corresponding pixel in the resulting images after the 4 convolutions (FIGS. 9A and 9B). For example, in FIG. 9A, 910 illustrates the image by thresholding and combining images 710, 720, 730, and 740 in FIG. 7. Performing the above steps results in obtaining populations 912, 914, 916, and 918.

Combined image 910 is later labeled as labeled image 920 by tagging each connected region with a unique label as shown in FIG. 9B. For example, in one embodiment of the present invention, different numeric values can be used as labels, such as 1, 2, 3, and 4 for the seed populations 922, 924, 926, and 928 in labeled image 920.

Setting Anchor Points

Once the seeds are detected, the next step is to set the anchor points using anchor point module 441. The anchor points provide the basis for the definition of a linear segmentation of the 2D image. In one embodiment, the anchor points are defined using the seeds detected by methods described above in the Seed Detection section.

In one embodiment, anchor point module 441 sets anchor points. In step 505, a set of seeds are identified by first separating the detected seed populations into groups by seed population separator module 438. Each seed is classified into a group (e.g., type of white cell population) expected to be found in the 2D projection under analysis. A predefined partition of the 2D image serves as a guideline for the assignment of each seed into a group. A seed landmark identifier module 439 then identifies a landmark seed population in each group. Criteria, such as seed location or density, can be used to select the most relevant seed population in a group as the landmark seed population. Seed populations other than the landmark seed populations in each group are deleted by seed population deletion module 440. In step 506, anchor point module 441 calculates statistics for each landmark seed population and determines the anchor points using the landmark seed populations.

Anchor point setting is customized for each image depending on the expected location of the different particle populations. In one embodiment, the anchor points are set as middle points of imaginary lines joining the centers of mass of any pair of selected seed populations. The center of mass of a seed population can be obtained by calculating the average coordinates of the pixels in the population in a thresholded image. Additional anchor points can be added to define a region of the image depending on a specific pattern expected in the image. Anchor points 1012 set based on the labeled 2D image 920 in FIG. 9 are shown in FIG. 10A. In image 1010 of FIG. 10A, points 1012 are example anchor points set by the above procedure according to one embodiment of the invention.

In step 507, a linear segmentation is defined based on the anchor points 1012 (FIG. 10) by segment generator 442. In image 1020 of FIG. 10B, for example, line segment 1022 is a segment line passing through anchor point 1012 set as described above with respect to image 1010. In one embodiment, the line segments are contour lines separating the seed populations. Each contour line has a set of contour points, which are sample points on the contour line.

Non-Linear Segmentation Based on Energy Minimization

In some embodiments, the actual lines of the linear segmentation can cut through a population. To avoid cutting through populations, contour points on the lines can be moved based on energy minimization techniques in step 508 by contour point adjustment module 443. Movements of the contour points are also constrained to avoid unusual occurrences including undue influence of higher intensity points, and points swapping that can form loops. For example, in an embodiment, the contour points in horizontal lines can only move +/−5 pixels in the vertical direction and contour points in vertical lines can only move +/−5 pixels in the horizontal direction.

In one embodiment, the contour points defining the line segments are input to the first non-linear energy based segmentation step termed active contouring. For example, in one embodiment, the active contouring is based on any of the models defined in "Snakes: active contour models", presented by Kass et al. in International Journal of Computer Vision 1 (1988) 321-331, which is incorporated herein by reference in its entirety.

The energy function E to be minimized is modified in this approach by replacing the gradient image term with the smoothed 2D image I(x,y) as defined in (11):

$$E = \frac{1}{2}\left[\alpha(s)\left|\frac{\partial v(s)}{\partial s}\right|^2 + \beta(s)\left|\frac{\partial^2 v(s)}{\partial s^2}\right|^2\right] + \gamma(s)I(x, y) \quad (11)$$

In the energy function defined in equation (11), v(s) defines the active contour, and α(s), β(s), and γ(s) are weight functions. The terms of the equation (11) correspond to energy E being a function of distance, curvature, and intensity. According to equation (11), pixels in the 2D image I(x,y) with high intensity values can increase the value of energy function E. Such pixels represent histogram bins with high number of events, i.e. high histogram amplitude. Similarly, pixels with low intensity values can decrease the value of energy function E. While locating points with minimal 2D histogram amplitude using this energy minimization technique with a controlled curvature, neighboring points on the active contour are kept as close as possible to reduce the distance. The minimization of equation (11) can be implemented by an iterative process. In one embodiment, the iterative minimization process is stopped after a predefined number of iterations. In another embodiment, the iterative minimization process is stopped when a minimum ratio or absolute change in the energy function between two successive iterations is below a predetermined threshold. In alternative embodiments, both stopping conditions are used. This active contouring step makes an initial non-linear segmentation of the 2D histogram.

Refining Non-Linear Segmentation

In some embodiments, the above-described non-linear segmentation can smoothly segment the 2D histogram into clusters. However, in other embodiments, additional refinement of the non-linear segmentation is required, for example, if the clusters are not well segmented. The refinement stage starts in step 509 by first creating a band around each contouring point using band definition module 444. A "band" is defined as a window around the current segmentation line (e.g, +/−5 pixels). The size of the band is case specific, and varies upon how much freedom is to be given to the refinement step. FIG. 11 illustrates an exemplary band (e.g., band 1130) created around each contouring point and the resulting isolated regions (e.g., regions 1112, 1114, 1116, 1118, and 1120) in image 1110.

The resulting bands create isolated regions which are later dilated by band dilation module 445. Dilation means merging some of the regions. Dilating the band image include two main steps: dual grayscale reconstruction and Watershed transformation.

Dual Grayscale reconstruction

After the bands are created, step 509 continues with dual grayscale reconstruction of the 2D band image by dual grayscale reconstruction module 446. Dual grayscale reconstruction is an image morphology operation that repeats grayscale geodesic erosion on the image until there is no more change or the change is less than a predefined amount. The input of dual grayscale reconstruction includes an inverted version of the smoothed 2D image and an inverted version of the corresponding band image. The first one is known as a mask image and the second is known as a marker image. For example, in FIG. 12, image 1210 is a three-dimensional (3D) view of a mask image 1220, where the intensity values are represented as a height function in the third dimension. Image 1230 is the 3D view of a marker image 1240.

FIGS. 13A and 13B show an exemplary result of this dual grayscale reconstruction procedure. In FIG. 13A, image 1310 is the reconstructed 3D image. In FIG. 13B, image 1320 is the reconstructed image using image 1220 and 1240.

Watershed Transformation

Once the dual grayscale reconstructed image is available, it is passed to the Watershed transformation in step 510. An example Watershed transformation is described in "Watersheds of functions and picture segmentation" by S. Beucher, published in Acoustics, Speech, and Signal Processing, IEEE International Conference on ICASSP, Volume 7, May 1982, Pages 1928-1931, which is incorporated herein by reference in its entirety. In one embodiment, the Watershed transformation is performed by Watershed transformation module 447. The Watershed transformation is a morphology-based image processing method that further refines segmentation of an image into regions based on the different amplitude values of the image. A basic explanation of the Watershed transformation is to view the process as a flooding process. Referring to FIGS. 13A and 13B, the Watershed transformation is initiated by "pouring" water into each independent "hole" until the water boundaries start to touch each other once they reach the surface. The result of applying this segmentation method can be seen in FIGS. 14A and 14B. In FIG. 14, an exemplary image 1410 is segmented into regions 1412, 1414, 1416, 1418 and 1420 by Watershed transformation. In FIG. 14B, the RLS-DC image 1430 is segmented accordingly with white cell populations 1432, 1434, 1436 and 1438. In image 1430, clusters 1432, 1434, and 1436 correspond to monocyte, neutrophil, and eosinophil populations, respectively. Cluster 1438 corresponds to lymphocyte and basophil populations, which are now more easily distinguished from other populations.

In one embodiment, the segmented results are displayed on a display such as a monitor, a projector screen, etc. In another embodiment, the segmented results are stored on a storage device such as a hard disk, a floppy disk, a flash drive, etc. The segmented results can also be used to improve counting the particles in the differentiated populations. These examples are illustrative and not intended to limit the present invention.

Embodiments of the present invention provide a method for segmenting 2D histograms for particle analysis. The segmentation is done on 2D histograms directly without consulting 1D histogram analysis. In one embodiment, the segmentation includes three steps: cluster detection by means of digital image filtering techniques; initial non-linear 2D region segmentation based on active contouring using the clusters detected in the previous step as the main source of information to place the initial models; and refinement of the active contour segmentation by means of morphology based image processing methods such as dual grayscale reconstruction and Watershed transformation. This method can improve the particle differentiation when overlapping and shifting occurs among particle populations. In one embodiment, the particles can be white blood cells where cell populations are overlapped and shifted due to abnormalities in the morphology or internal structure of the cells. Based on the presented method, embodiments of the present invention can handle complex abnormal blood samples and more accurately report white cell percentages in such cases.

Exemplary Computer Systems

In some embodiments, analysis system 430 and its components can be implemented using hardware, firmware, software or a combination thereof and can be implemented in a computing device such as a computer system. In an embodiment, an exemplary computer system 1500, is shown in FIG. 15. Computer system 1500 includes one or more processors, such as processor 1504. Processor 1504 is connected to a communication infrastructure 1506 (such as a bus).

Computer system 1500 also includes a main memory 1508, preferably random access memory (RAM), and can also include a secondary memory 1510. Secondary memory 1510 can include, for example, a hard disk drive 1512 and/or a removable storage drive 1514, representing a floppy disk drive, an optical disk drive, etc. Removable storage drive 1514 reads from and/or writes to a removable storage unit 1518 in a well-known manner. Removable storage unit 1518, represents a floppy disk, optical disk, memory card, etc. which is read by and written to by removable storage drive 1514. As will be appreciated, the removable storage unit 1518 includes a computer usable storage medium having stored therein computer software and/or data.

In alternative embodiments, secondary memory 1510 can include other similar means, such as a removable storage unit 1522 and an interface 1520, for allowing computer programs or other instructions to be loaded into computer system 1500. Examples of such can include a program cartridge and cartridge interface (such as that found in video game devices), a removable memory chip (such as an EPROM, or PROM) and associated socket, and other removable storage units and interfaces.

Computer system 1500 can also include a communication interface 1524. Communication interface 1524 enables computer 1500 to communicate with external and/or remote devices. Examples of communications interface 1524 can include a modem, a network interface (such as an Ethernet card), a communications port, a PCMCIA slot and card, etc. Computer system 1500 receives data and/or computer program products via communication network 1524. Software and data can be transferred via communications interface 1524.

Computer programs (also called computer control logic) are stored in main memory 1508 and/or secondary memory 1510. Computer programs can also be received via communications interface 1524 and/or signals 1528. Such computer programs, when executed, enable computer system 1500 to perform the features of the present invention as discussed herein. In particular, the computer programs, when executed, enable processor 1504 to perform the features of embodiments of the present invention. Accordingly, such computer programs represent controllers of computer system 1500.

In an embodiment where the invention is implemented using software, the software can be stored in a computer program product having a tangible computer readable medium and loaded into computer system 1500 using removable storage drive 1514, hard disk drive 1512 or communications interface 1524. The control logic (software), when executed by processor 1504, causes processor 1504 to perform the functions of embodiments of the invention as described herein.

Computer 1500 also includes input/output/display devices 1532, such as one or more monitors, keyboards, pointing devices, etc.

While various embodiments of the present invention have been described above, it should be understood that they have been presented by way of example, and not limitation. It will be apparent to persons skilled in the relevant computer arts that various changes in form and detail can be made therein without departing from the spirit and scope of the invention. Furthermore, it should be appreciated that the detailed description of the present invention provided herein, and not the summary and abstract sections, is intended to be used to interpret the claims. The summary and abstract sections can set forth one or more but not all exemplary embodiments of the present invention as contemplated by the inventors. Embodiments can work with software, hardware, and operating system implementations other than those described herein. Any software, hardware, and operating system implementations suitable for performing the functions described herein can be used. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalence.

What is clamed is:

1. A method for determining a population of particles contained in a biological sample, comprising:
   (a) passing particles from the biological sample through a measuring region of a particle analyzer;
   (b) interrogating each particle passing through the measuring region with respect to at least two parameters;
   (c) detecting the at least two parameters with one or more detectors;
   (d) storing the detected at least two parameters as data;
   (e) selecting first data stored for a first parameter and a second data stored for a second parameter;
   (f) creating an initial two-dimensional histogram using the selected data for the first and second parameters, wherein a first dimension of the two-dimensional histogram corresponds to the first parameter and a second dimension of the two-dimensional histogram corresponds to the second parameter;
   (g) filtering the initial two-dimensional histogram to generate a filtered two-dimensional image;
   (h) detecting a plurality of seed populations in the filtered two-dimensional image;
   (i) determining one or more anchor points and generating one or more linear contour lines to separate the detected seed populations, the contour lines running though the one or more anchor points, each contour line having a plurality of contour points; and
   (j) adjusting the contour points in at least one of the linear contour lines to separate the detected seed populations.

2. The method of claim 1, wherein the biological sample is a blood sample and step (a) comprises passing blood cells from the blood sample.

3. The method of claim 1, wherein step (a) comprises passing the particles from the biological sample through a measuring region of a flow cytometer or hematology analyzer.

4. The method of claim 1, wherein step (g) comprises removing per-pixel noise in the two-dimensional histogram.

5. The method of claim 4, wherein step (g) comprises:
   selecting a set of one or more pixels in the two-dimensional histogram; and
   for each pixel in the selected set:
       discarding the pixel if the pixel does not have a predefined number of neighboring pixels having a non-zero value and does not have a value corresponding to at least a predetermined number of events.

6. The method of claim 4, wherein step (g) comprises:
selecting a set of one or more pixels in the two-dimensional histogram;
and for each pixel in the selected set:
discarding the pixel if the pixel does not have a predefined number of neighboring pixels having a non-zero value; or
discarding the pixel if the pixel does not have a value corresponding to at least a predetermined number of events.

7. The method of claim 1, wherein step (g) comprises applying a smoothing filter at least once.

8. The method of claim 1, wherein step (g) comprises applying at least one edge detection filter to the filtered two-dimensional image to generate a final edge-detected two-dimensional image.

9. A method for determining a population of particles contained in a biological sample, comprising:
(a) passing particles from the biological sample through a measuring region of a particle analyzer;
(b) interrogating each particle passing through the measuring region with respect to at least two parameters;
(c) detecting the at least two parameters with one or more detectors;
(d) storing the detected at least two parameters as data;
(e) selecting first data stored for a first parameter and a second data stored for a second parameter;
(f) creating an initial two-dimensional histogram using the selected data for the first and second parameters, wherein a first dimension of the two-dimensional histogram corresponds to the first parameter and a second dimension of the two-dimensional histogram corresponds to the second parameter;
(g) filtering the initial two-dimensional histogram to generate a filtered two-dimensional image;
(h) detecting a plurality of seed populations in the filtered two-dimensional image;
(i) generating one or more linear contour lines, each having a plurality of contour points, to separate the detected seed populations; and
(j) adjusting the contour points in at least one of the linear contour lines to separate the detected seed populations,
wherein step (g) further comprises
applying a plurality of edge detection filters to the filtered two-dimensional image to generate a plurality of intermediate edge-detected two-dimensional images; and
combining the plurality of intermediate edge-detected two-dimensional images to generate the final edge-detected two-dimensional image.

10. The method of claim 9, wherein combining the plurality of intermediate edge-detected two-dimensional images, comprises:
thresholding each of the intermediate edge-detected two-dimensional images; and
performing a pixel-by-pixel logical AND operation to generate the edge-detected two-dmensional image.

11. The method of claim 1, wherein step (h) further comprises:
separating the detected seed populations into groups having one or more detected seed populations;
identifying a landmark seed population in each group; and
deleting each seed population in each group that is not the landmark seed population.

12. The method of claim 1 wherein determining the anchor points comprises:
applying a predetermined segmentation to the seed populations;
determining a landmark seed population in at least one area defined by the applied segmentation;
calculating at least one statistic for each landmark seed population; and
determining the anchor points using the landmark seed populations.

13. A method for determining a population of particles contained in a biological sample, comprising:
(a) passing particles from the biological sample through a measuring region of a particle analyzer;
(b) interrogating each particle passing through the measuring region with respect to at least two parameters;
(c) detecting the at least two parameters with one or more detectors;
(d) storing the detected at least two parameters as data;
(e) selecting first data stored for a first parameter and a second data stored for a second parameter;
(f) creating an initial two-dimensional histogram using the selected data for the first and second parameters, wherein a first dimension of the two-dimensional histogram corresponds to the first parameter and a second dimension of the two-dimensional histogram corresponds to the second parameter;
(g) filtering the initial two-dimensional histogram to generate a filtered two-dimensional image;
(h) detecting a plurality of seed populations in the filtered two-dimensional image;
(i) generating one or more linear contour lines, each having a plurality of contour points, to separate the detected seed populations; and
(j) adjusting the contour points in at least one of the linear contour lines to separate the detected seed populations,
wherein step (j) further comprises adjusting the contour points to minimize an energy function.

14. A method for determining a population of particles contained in a biological sample, comprising:
(a) passing particles from the biological sample through a measuring region of a particle analyzer;
(b) interrogating each particle passing through the measuring region with respect to at least two parameters;
(c) detecting the at least two parameters with one or more detectors;
(d) storing the detected at least two parameters as data;
(e) selecting first data stored for a first parameter and a second data stored for a second parameter;
(f) creating an initial two-dimensional histogram using the selected data for the first and second parameters, wherein a first dimension of the two-dimensional histogram corresponds to the first parameter and a second dimension of the two-dimensional histogram corresponds to the second parameter;
(g) filtering the initial two-dimensional histogram to generate a filtered two-dimensional image;
(h) detecting a plurality of seed populations in the filtered two-dimensional image;
(i) generating one or more linear contour lines, each having a plurality of contour points, to separate the detected seed populations; and
(j) adjusting the contour points in at least one of the linear contour lines to separate the detected seed populations,
wherein step (j) further comprises defining a band around each contour point.

15. The method of claim 14, wherein step (j) further comprises dilating each defined band around each contour point.

16. The method of claim 15, wherein the dilating comprises:

performing dual grayscale reconstruction on the filtered two-dimensional image; and applying a Watershed transformation on the dual-grayscale-reconstructed image.

17. The method of claim 16, wherein performing the dual grayscale reconstruction comprises:

inverting the filtered two-dimensional image;

creating a band image using a portion of the filtered two-dimensional image corresponding to the bands; and performing geodesic erosion on the band image to obtain a dual grayscale reconstructed image.

18. The method of claim 17, wherein applying the Watershed transformation comprises:

combining the dual grayscale reconstructed image with the band image to obtain a combined result two-dimensional image; and inputting the combined result two-dimensional image to a Watershed transformation function to further refine segmentation.

19. The method of claim 1, further comprising displaying the contour lines with the adjusted contour points.

20. The method of claim 1, further comprising storing the contour lines with the adjusted contour points.

21. The method of claim 1, further comprising counting particles in each seed population separated by the contour lines with the adjusted contour points.

22. The method of claim 1, wherein step (c) comprises detecting at least two parameters selected from the following group of parameters: direct current, volume, radiofrequency, opacity, one or more types of light scatter, axial light loss, and fluorescence.

23. A device for analyzing particles from a biological sample, comprising:

at least one detector configured to detect at least two parameters corresponding to a particle from a biological sample interrogated by a plurality of interrogation sources;

at least one processor in communication with the at least one detector, the processor configured to receive data representing the at least two parameters detected by the at least one detector from a biological sample interrogated by the plurality of interrogation sources; and a memory in communication with the at least one processor and configured to store the data corresponding to the parameters;

the at least one processor configured to select first data corresponding to a first stored parameter and second data corresponding to a second stored parameter;

the at least one processor further configured to create an initial two-dimensional histogram using data corresponding to the first and second parameters, wherein a first dimension of the two-dimensional histogram corresponds to the first parameter, and a second dimension of the two-dimensional histogram corresponds to the second parameter;

the at least one processor further configured to apply a filter to the initial two-dimensional histogram to generate a filtered two-dimensional image;

the at least one processor further configured to detect a plurality of seed populations in the filtered two-dimensional image;

the at least one processor further configured to generate one or more anchor points and one or more linear contour lines running through the one or more anchor points, the contour lines separating the detected seed populations, each contour line having a plurality of contour points; and the at least one processor further configured to adjust the contour points of at least one of the linear contour lines to separate the detected seed populations.

24. The device of claim 23, wherein the at least one processor is further configured to filter pixels in the initial two-dimensional histogram to reduce per-pixel noise in the two-dimensional histogram.

25. The device of claim 24, wherein the at least one processor is further configured to:

select a set of pixels in the two-dimensional histogram; and for each pixel in the set:

discard the pixel if the selected pixel does not have a number of neighboring pixels that have a nonzero value and the selected pixel does not have a value corresponding to at least a particular number of events.

26. The device of claim 24, wherein the at least one processor is further configured to:

select a set of pixels in the two-dimensional histogram; and for each pixel in the set:

discard the pixel if the selected pixel does not have a number of neighboring pixels that have a nonzero value; or discard the pixel if the selected pixel does not have a value corresponding to at least a particular number of events.

27. The device of claim 23, wherein the at least one processor is further configured to apply a smoothing filter to the two-dimensional histogram at least once.

28. The device of claim 23, wherein the at least one processor is further configured to apply at least one edge detection filter to the filtered two-dimensional image to generate a final edge-detected two-dimensional image.

29. A device for analyzing particles from a biological sample, comprising:

at least one detector configured to detect at least two parameters corresponding to a particle from a biological sample interrogated by a plurality of interrogation sources;

at least one processor in communication with the at least one detector, the processor configured to receive data representing the at least two parameters detected by at least one detector from a biological sample interrogated by a plurality of interrogation sources; and a memory in communication with the at least one processor and configured to store the data corresponding to the parameters;

the at least one processor configured to select first data corresponding to a first stored parameter and second data corresponding to a second stored parameter;

the at least one processor further configured to create an initial two-dimensional histogram using data corresponding to the first and second parameters, wherein a first dimension of the two-dimensional histogram corresponds to the first parameter, and a second dimension of the two-dimensional histogram corresponds to the second parameter;

the at least one processor further configured to apply a filter to the initial two-dimensional histogram to generate a filtered two-dimensional image;

the at least one processor further configured to detect a plurality of seed populations in the filtered two-dimensional image;

the at least one processor further configured to generate one or more linear contour lines that separate the detected seed populations, each contour line having a plurality of contour points; and the at least one processor further configured to adjust the contour points of at least one of the linear contour lines to separate the detected seed populations, wherein the at least one processor is further configured to apply a plurality of edge detection filters to the filtered two-dimensional image to generate a plurality of intermediate edge-detected two-dimensional images; and the at least one processor is further configured to combine the plurality of intermediate edge-detected two-dimensional images to form the final edge-detected two-dimensional image.

30. The device of claim 29, wherein combining the plurality of intermediate edge-detected two-dimensional images further comprises thresholding each of the intermediate edge-detected two-dimensional images to generate a plurality of thresholded two-dimensional images; and applying a logical AND operator to logically AND the generated thresholded two-dimensional images on a pixel-by-pixel basis.

31. The device of claim 23, wherein the at least one processor is further configured to separate the detected seed populations into groups having one or more detected seed populations, to identify a landmark seed population in each group, and to delete each seed population in each group that is not the landmark seed population.

32. A device for analyzing particles from a biological sample, comprising:

at least one detector configured to detect at least two parameters corresponding to a particle from a biological sample interrogated by a plurality of interrogation sources;

at least one processor in communication with the at least one detector, the processor configured to receive data representing the at least two parameters detected by at least one detector from a biological sample interrogated by a plurality of interrogation sources; and a memory in communication with the at least one processor and configured to store the data corresponding to the parameters;

the at least one processor configured to select first data corresponding to a first stored parameter and second data corresponding to a second stored parameter;

the at least one processor further configured to create an initial two-dimensional histogram using data corresponding to the first and second parameters, wherein a first dimension of the two-dimensional histogram corresponds to the first parameter, and a second dimension of the two-dimensional histogram corresponds to the second parameter;

the at least one processor further configured to apply a filter to the initial two-dimensional histogram to generate a filtered two-dimensional image;

the at least one processor further configured to detect a plurality of seed populations in the filtered two-dimensional image;

the at least one processor further configured to generate one or more linear contour lines that separate the detected seed populations, each contour line having a plurality of contour points; and the at least one processor further configured to adjust the contour points of at least one of the linear contour lines to separate the detected seed populations, and wherein the at least one processor is further configured to determine one or more anchor points for defining the contour lines, apply a predetermined segmentation to the seed populations, determine a landmark seed population in at least one area defined by the applied segmentation, calculate at least one statistic for each landmark seed population, and determine the anchor points using the landmark seed populations.

33. The device of claim 23, wherein the at least one processor is further configured to generate at least one linear segment comprising a plurality of contour points, and to adjust the contour points to minimize an energy function.

34. The device of claim 23, wherein the at least one processor is further configured to define a band around each contour point.

35. The device of claim 34, wherein the at least one processor is further configured to dilate each defined band around each contour point.

36. The device of claim 35, wherein the at least one processor is further configured to perform dual grayscale reconstruction on the edge-detected image, and to apply a Watershed transformation on the dual grayscale reconstructed image.

37. The device of claim 36, wherein the at least one processor is further configured to:

invert the edge-detected two-dimensional image, create a band image using a portion of the edge-detected two-dimensional image corresponding to the bands, and perform geodesic erosion on the band image to obtain a dual grayscale reconstructed image.

38. The device of claim 37, wherein the at least one processor is further configured to:

combine the dual grayscale reconstructed image with the band image to obtain a combined resulting two-dimensional image, and input the combined resulting two-dimensional image to a Watershed transformation function to further refine segmentation.

39. The device of claim 23, wherein the at least two parameters comprise at least two parameters selected from the following group of parameters: direct current, volume, radiofrequency, opacity, one or more types of light scatter, axial light loss, and fluorescence for the sample of the particles.

* * * * *